(12) United States Patent
Jin et al.

(10) Patent No.: US 10,113,976 B2
(45) Date of Patent: Oct. 30, 2018

(54) METHOD AND DEVICE FOR NON-CONTACT DETECTION OF THIN MEDIUM

(71) Applicant: GRG BANKING EQUIPMENT CO., LTD., Guangzhou, Guangdong (CN)

(72) Inventors: Xiaofeng Jin, Guangdong (CN); Jianping Liu, Guangdong (CN); Tiancai Liang, Guangdong (CN); Wenchuan Gong, Guangdong (CN)

(73) Assignee: GRG BANKING EQUIPMENT CO., LTD., Guangzhou, Guangdong (CN)

( * ) Notice: Subject to any disclaimer, the term of this patent is extended or adjusted under 35 U.S.C. 154(b) by 0 days.

(21) Appl. No.: 15/523,203

(22) PCT Filed: Jul. 8, 2015

(86) PCT No.: PCT/CN2015/083512
§ 371 (c)(1),
(2) Date: Apr. 28, 2017

(87) PCT Pub. No.: WO2016/070643
PCT Pub. Date: May 12, 2016

(65) Prior Publication Data
US 2017/0315063 A1    Nov. 2, 2017

(30) Foreign Application Priority Data
Nov. 4, 2014 (CN) .......................... 2014 1 0617820

(51) Int. Cl.
*G01B 11/02* (2006.01)
*G01N 21/892* (2006.01)
(Continued)

(52) U.S. Cl.
CPC ........... *G01N 21/892* (2013.01); *G01B 11/14* (2013.01); *G01N 21/8806* (2013.01);
(Continued)

(58) Field of Classification Search
CPC .. G01N 21/892; G01N 21/8806; G01N 21/94; G01N 21/8422; G01N 21/45;
(Continued)

(56) References Cited

U.S. PATENT DOCUMENTS 5,988,345 A    11/1999    Bergeron et al.
2003/0156294 A1    8/2003    D'Agraives et al.
(Continued)

FOREIGN PATENT DOCUMENTS

CN    1614457 A    5/2005
CN    201050978 Y    4/2008
(Continued)

OTHER PUBLICATIONS

Extended European Search Report for corresponding Application No. 15857062.2 dated Oct. 11, 2017.
(Continued)

*Primary Examiner* — Tarifur Chowdhury
*Assistant Examiner* — Jonathon Cook
(74) *Attorney, Agent, or Firm* — U.S. Fairsky LLP; Yue (Robert) Xu

(57) ABSTRACT

A method and device for non-contact detection of a thin medium (5) is disclosed. The device comprises a light source (1), an optical splitter (2), a reference plane (3), a linearly arrayed photoelectric detector (6), a signal processing module (4) and the thin medium (5). The method involves the following steps: acquiring time for targeted light which is emitted by the light source (1) and reflected by the thin medium (5) to the linearly arrayed photoelectric detector (6), and acquiring time for reference light which is emitted by the light source (1) and reflected by the reference plane (3) to the linearly arrayed photoelectric detector (6); according to the acquired time that the targeted light and the reference light arrive at the linearly arrayed photoelectric detector (6),
(Continued)

computing a first optical path and a second optical path corresponding to the targeted light and the reference light respectively, and acquiring quantity of bright fringes and dark fringes of interference fringes according to a predetermined computing manner by the signal processing module (4); conducting difference comparison between the quantity of the bright fringes and dark fringes of the interference fringes and the quantity of the bright fringes and dark fringes of standard interference fringes according to the predetermined manner, and if the value of the comparison result is larger than the predetermined threshold value, determining that the foreign matters are positioned on the thin medium (5). The detection method and device solves the technical problems that precision is low and measuring wavelength is long caused by an existing mechanical thickness measuring device, an infrared detector and an ultrasonic detector used to detect the foreign substance on the surface of the thin medium.

8 Claims, 3 Drawing Sheets

(51) Int. Cl.
    *G01N 21/94*     (2006.01)
    *G01B 11/14*     (2006.01)
    *G01N 21/88*     (2006.01)
    *G07D 7/12*     (2016.01)
    *G07D 7/164*     (2016.01)
    *G07D 7/189*     (2016.01)

(52) U.S. Cl.
    CPC ............... *G01N 21/94* (2013.01); *G07D 7/12* (2013.01); *G07D 7/164* (2013.01); *G07D 7/189* (2017.05)

(58) Field of Classification Search
    CPC ............ G01N 2021/8427; G01B 11/06; G01B 11/0616; G01B 11/0675; G01B 11/2441; G01B 11/14; G01B 9/02088
    USPC ......................................... 356/498, 503, 504
    See application file for complete search history.

(56) References Cited

U.S. PATENT DOCUMENTS

| | | |
|---|---|---|
| 2007/0153286 A1 | 7/2007 | Hughes et al. |
| 2012/0120485 A1 | 5/2012 | Ootomo et al. |
| 2012/0127473 A1 | 5/2012 | Pfaff et al. |
| 2012/0176624 A1 | 7/2012 | Mansfield |
| 2014/0218734 A1 | 8/2014 | Shimaoka et al. |

FOREIGN PATENT DOCUMENTS

| | | |
|---|---|---|
| CN | 101261116 A | 9/2008 |
| CN | 101319872 A | 12/2008 |
| CN | 101379891 A | 3/2009 |
| CN | 101551327 A | 10/2009 |
| CN | 102472608 A | 5/2012 |
| CN | 103765483 A | 4/2014 |
| CN | 104297260 A | 1/2015 |
| CN | 202041181 U | 11/2016 |
| DE | 19704496 A1 | 3/1998 |
| JP | 2009300279 A | 12/2009 |
| WO | 2013050931 A1 | 4/2013 |

OTHER PUBLICATIONS

International Search Report for PCT/CN2015/083512, dated Oct. 9, 2015, ISA/CN.

The Russian 1st Office Action dated Apr. 26, 2018 and the English Translation for RU2017118452.

METHOD AND DEVICE FOR NON-CONTACT DETECTION OF THIN MEDIUM

CROSS REFERENCE OF RELATED APPLICATION

The application is the national phase of International Application No. PCT/CN2015/083512, titled "METHOD AND DEVICE FOR NON-CONTACT DETECTION OF THIN MEDIUM", and filed on Jul. 8, 2015, which claims the priority to Chinese Patent Application No. 201410617820.5, titled "METHOD AND DEVICE FOR NON-CONTACT DETECTION OF THIN MEDIUM", filed with the Chinese State Intellectual Property Office on Nov. 4, 2014, the entire disclosure of which is incorporated herein by reference.

FIELD

The present disclosure relates to the technical field of photoelectric detection, and in particular to a method and a device for non-contact detection of a thin medium.

BACKGROUND

In a daily life and business activity, corner missing and tearing and so on of a banknote generally occur during a using process, and people generally bond the damaged or torn banknote using an adhesive tape or using a thin paper together with glue or the like, so as to continue to use the banknote. It is difficult to detect a banknote of which a surface is bonded with a foreign body effectively using a conventional mechanical apparatus. The banknote bonded with the foreign body is likely to result in damaging of a counterfeit detector and a sorting and identifying apparatus in a bank. If the banknote bonded with the foreign body is detected manually, it results in a waste of manpower and time and low detection efficiency. The financial industry proposes a requirement of "a quality of the circulated RMB should be superior than 70% of a quality of the new issued banknote" under support from the country, which requires financial self-service apparatus to improve the capability and level for identifying a banknote.

The conventional methods for detecting a foreign body on a surface of a banknote is by using a mechanical thickness measurement device, an infrared detection device or an ultrasound detection device. The mechanical thickness measurement device is difficult to detect a thin foreign body on the surface of the banknote due to low measurement accuracy. The infrared detection device has narrow application fields, and can detect only foreign bodies on the surface of the banknote having different directions and different reflection characteristics, such as transparent adhesive tapes. The ultrasound detection device has a long measurement wavelength and low accuracy due to using ultrasound as a carrier.

SUMMARY

According to embodiments of the present disclosure, a method and a device for non-contact detection of a thin medium are provided, which solve a technical problem of low accuracy and a long measurement wavelength when it is detected whether there is a foreign body on a surface of a thin medium using the existing mechanical thickness measurement device, infrared detection device and ultrasound detection device.

According to an embodiment of the present disclosure, a method for non-contact detection of a thin medium is provided, which includes:

step S1, obtaining time instants when target light, which is generated by reflecting light emitted by a light source via the thin medium, reaches a linear array photoelectric detector;

step S2, obtaining time instants when reference light, which is generated by reflecting the light emitted by the light source via a reference plane, reaches the linear array photoelectric detector;

step S3, calculating first optical distances and second optical distances corresponding to the target light and the reference light based on the obtained time instants when the target light and the reference light reach the linear array photoelectric detector, and obtaining, by a signal processing module through using a predetermined calculation method, the number of bright and dark fringes in interference fringes; and step S4, calculating a difference between the number of the bright and dark fringes in the interference fringes and a standard number of bright fringes and dark fringes in interference fringes by using a predetermined method, and determining that there is a foreign body on a surface of the thin medium in a case that the difference is greater than a predetermined threshold.

Optionally, before step S1, the method may further include:

turning on the light source, where the light emitted by the light source is divided, by an optical splitter, into first light reflected to the thin medium and second light transmitted to the reference plane, where, the first light is reflected by the thin medium to generate the target light; and the second light is reflected back to the optical splitter by the reference plane and is reflected by the optical splitter to generate the reference light.

Optionally, the predetermined threshold may be determined based on an oldest thin medium and a standard thin medium by using a method of maximum difference.

Optionally, step S3 may include:

calculating the first optical distances of the target light according to a first formula in combination with the time instants when the target light reaches the linear array photoelectric detector, and calculating the second optical distances of the reference light according to a second formula in combination with the time instants when the reference light reaches the linear array photoelectric detector;

calculating the numbers of changes between the bright and dark fringes of the interference fringes according to a third formula based on the first optical distances, the second optical distances and the number of photosensitive units in the linear array photoelectric detector; and calculating an average value of the numbers of changes between the bright and dark fringes of the interference fringes for the numbers of changes between the bright and dark fringes of the interference fringes according to a fourth formula.

Optionally, step S4 may include:

obtaining a difference between the average value of the number of changes between the bright and dark fringes of the interference fringes and an average value of the number of changes between bright and dark fringes in interference fringes; and comparing the difference with the predetermined threshold; determining that there is a foreign body on the surface of the thin medium in a case that a comparison result is greater than the predetermined threshold; and determining that there is no foreign body on the surface of the thin medium in a case that the comparison result is not greater than the predetermined threshold and not less than zero.

Optionally, the first formula for calculating the first optical distances may be $\Delta_1 = ct_1$;

the second formula for calculating the second optical distances may be $\Delta_2 = ct_2$, where t1 indicates a time period from a time instant of turning on the light source to a time instant when the target light reaches the linear array photoelectric detector, and t2 indicates a time period from the time instant of turning on the light source to a time instant when the reference light reaches the linear array photoelectric detector;

the third formula for calculating the numbers of bright and dark fringes in interference fringes may be $$K(M, N) = \frac{\Delta_2 - \Delta_1}{\lambda_0},$$

where M indicates the total number of rows scanned by a light signal from the light source, N indicates the number of photosensitive units in the linear array photoelectrical detector, and $\lambda_0$ indicates a wavelength of the light source; and the fourth formula for calculating the average value of the numbers of changes between the bright and dark fringes of the interference fringes may be $$\Phi_2 = \frac{\sum_{i=1}^{M} \sum_{j=1}^{N} K(M, N)}{M \times N}.$$

According to an embodiment of the present disclosure, a device for non-contact detection of a thin medium is provided, which includes a light source, an optical splitter, a reference plane, a linear array photoelectric detector, a signal processing module and the thin medium, where the light source, the optical splitter and the reference plane are located at a same horizontal line;

the signal processing module, the linear array photoelectric, the optical splitter and the thin medium are located at a same vertical line;

the linear array photoelectric detector is located between the signal processing module and the optical splitter; and the optical splitter is sloped.

Optionally, the light source may be configured to emit light to the optical splitter, where the optical splitter divides the light into first light reflected to the thin medium and second light transmitted to the reference plane;

the thin medium may be configured to reflect the first light to the signal processing module to extract a signal;

the reference plane may be configured to reflect the second light to the optical splitter, where the optical splitter guides the second light to the signal processing module to extract a signal; and the linear array photoelectrical detector is installed above the signal processing module and configured to record time instants when target light and reference light reach the linear array photoelectric detector respectively after the light source is turned on.

Optionally, the device for non-contact detection of a thin medium may further include:

a transparent component placed below the thin medium; and a lens array installed between the linear array photoelectric detector and the optical splitter.

Optically, the device for non-contact detection of a thin medium may further include:

an external frame, where the light source and the reference plane are installed on two inner walls of the external frame respectively, the transparent component placed below the thin medium is arranged on top of the external frame, an inner groove is provided at inner bottom of the external frame, and the linear array photoelectric detector is arranged in the inner groove; and the signal processing module is arranged at bottom of the external frame.

It can be seen from the above technical solutions that, the embodiments of the present disclosure have the following advantages.

According to the embodiments of the present disclosure, a method and a device for non-contact detection of a thin medium are provided, where the method includes: step S1, obtaining time instants when target light, which is generated by reflecting light emitted by a light source via the thin medium, reaches a linear array photoelectric detector; step S2, obtaining time instants when reference light, which is generated by reflecting the light emitted by the light source via a reference plane, reaches the linear array photoelectric detector; step S3, calculating first optical distances and second optical distances corresponding to the target light and the reference light based on the obtained time instants when the target light and the reference light reach the linear array photoelectric detector, and obtaining, by a signal processing module through using a predetermined calculation method, the number of bright and dark fringes in interference fringes by a signal processing module; and step S4, calculating a difference between the number of the bright and dark fringes in the interference fringes and a standard number of bright fringes and dark fringes in interference fringes by using a predetermined method, and determining that there is a foreign body on a surface of the thin medium in a case that the difference is greater than a predetermined threshold. In the embodiment, the first optical distances and the second optical distances corresponding to the target light and the reference light are calculated based on the obtained time instants when the target light and the reference light reach the linear array photoelectric detector; the number of the bright and dark fringes in the interference fringes is obtained by the signal processing module through using the predetermined calculation method; the difference between the obtained number of the bright and dark fringes in the interference fringes and the standard number of bright and dark fringes in interference fringes is calculated in the predetermined manner; and it is determined that there is a foreign body on the surface of the thin medium in a case that the difference is greater than the predetermined threshold. With the above technical solutions, the following technical problems are solved: when it is detected whether there is a foreign body on the surface of the thin medium using the existing mechanical thickness measurement device, infrared detection device and ultrasound detection device, it is difficult to detect a thin foreign body on a surface of a banknote effectively due to low measurement accuracy of the mechanical thickness measurement device; only foreign bodies on the surface of the banknote having different directions and different reflection characteristics can be detected due to a narrow application field of the infrared detection device; and the ultrasound detection device has a long measurement wavelength and low measurement accuracy due to using ultrasound as a carrier.

BRIEF DESCRIPTION OF THE DRAWINGS

In order to illustrate technical solutions in embodiments of the present disclosure or the conventional technology more clearly, drawings for description of the embodiments or the conventional technology are introduced simply hereinafter. Apparently, the drawings described below only describe some embodiments of the present disclosure. Other drawings may be obtained according these drawings by those skilled in the art without any creative work.

Figure 3:
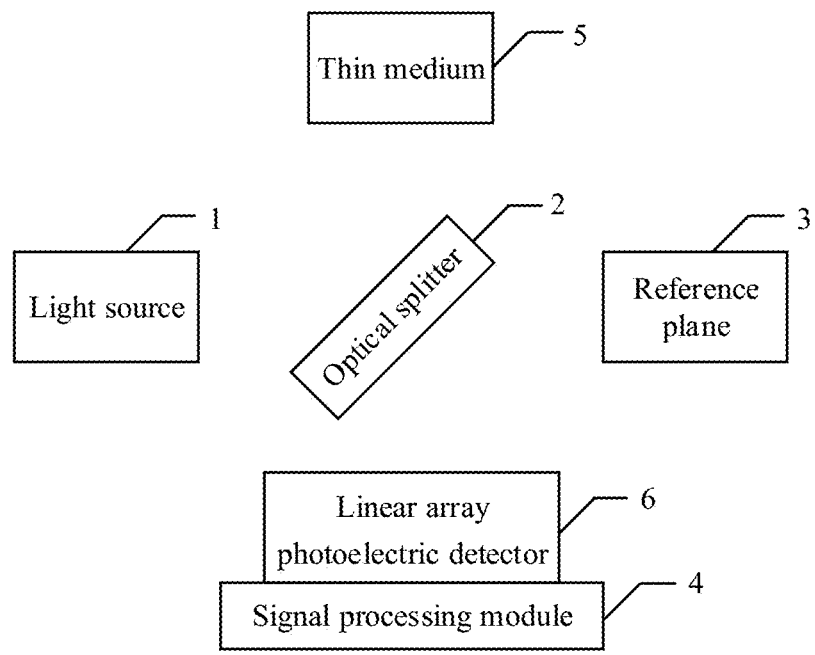
FIG. 3 is a schematic structural diagram of a device for non-contact detection of a thin medium according to an embodiment of the present disclosure.
Figure 4:
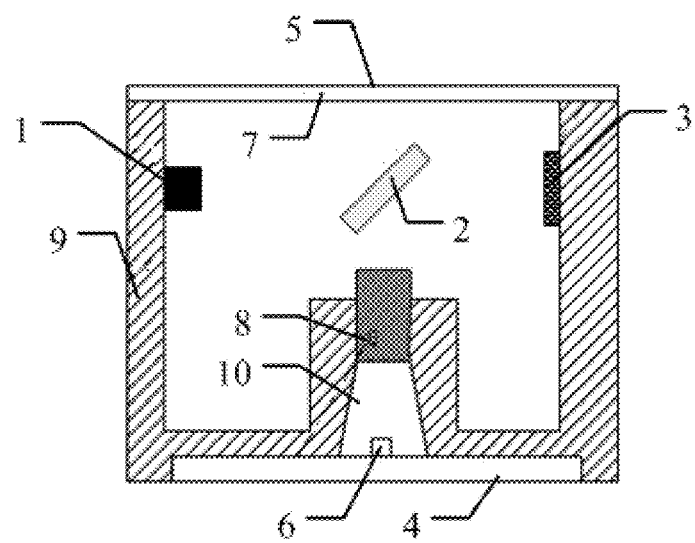
FIG. 4 is a schematic structural diagram of a device for non-contact detection of a thin medium according to another embodiment of the present disclosure.

Illustration for reference numerals in FIG. 3 and FIG. 4:
1 light source; 2 optical splitter; 3 reference plane; 4 signal processing module;
5 thin medium; 6 linear array photoelectric detector; 7 transparent component;
8 lens array; 9 external frame; 10 inner groove.

DETAILED DESCRIPTION

According to embodiments of the present disclosure, a method and a device for non-contact detection of a thin medium are provided, which solve a technical problem of low accuracy and a long measurement wavelength when it is detected whether there is a foreign body on a surface of the thin medium using the existing mechanical thickness measurement device, infrared detection device and ultrasound detection device.

In order to make objects, features and advantages of the present disclosure become clearer and easier to be understood, technical solutions in embodiments of the present disclosure are described clearly and completely in combination with drawings in the embodiments of the present disclosure hereinafter. Apparently, the embodiments described in the following only describe some rather than all of embodiments of the invention. Any other embodiments obtained based on the embodiments of the present disclosure by those skilled in the art without any creative work fall within the scope of protection of the present disclosure.

Figure 1:
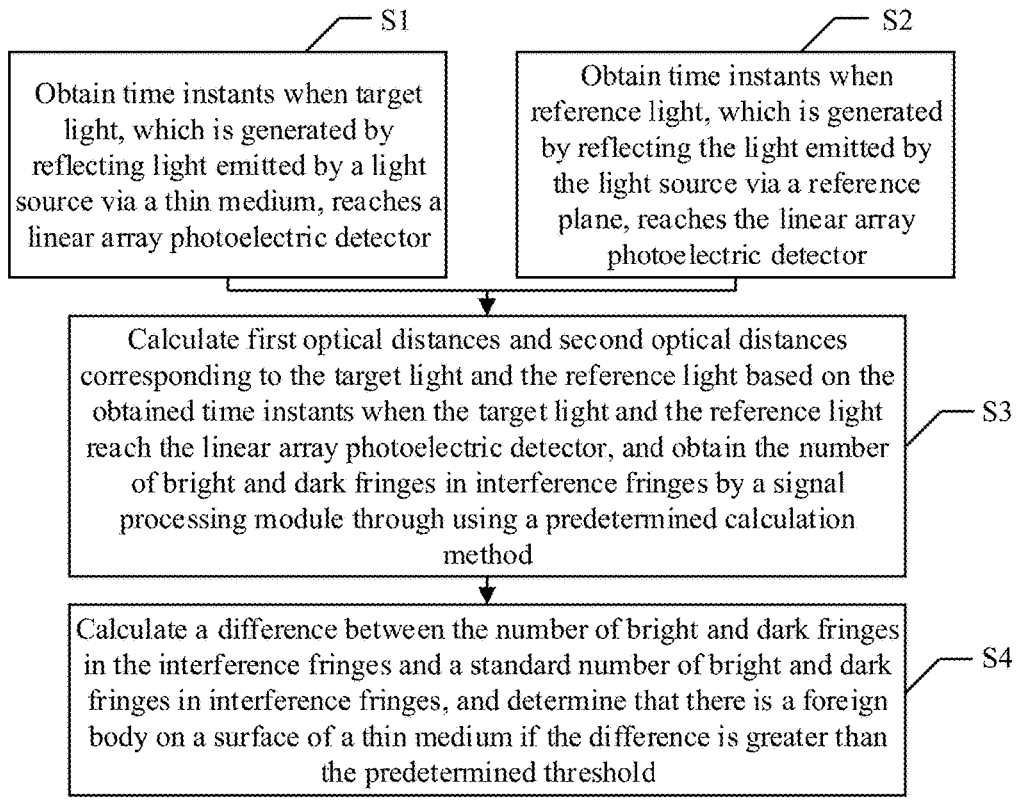
FIG. 1 is a schematic flowchart of a method for non-contact detection of a thin medium according to an embodiment of the present disclosure.

Referring to FIG. 1, a method for non-contact detection of a thin medium is provided according to an embodiment of the present disclosure. The method includes step S1 to step S4 in the following.

In step S1, time instants when target light, which is generated by reflecting light emitted by a light source via a thin medium, reaches a linear array photoelectric detector are obtained.

In the embodiment, when it is detected whether there is a foreign body on a surface of a thin medium such as a banknote, first it is needed to obtain the time instants when the target light, which is generated by reflecting the light emitted by the light source via the thin medium, reaches the linear array photoelectric detector. The time instants may be obtained by the linear array photoelectric detector. The light source described above may be a laser light source, and may further be a linear array laser light source.

In step S2, time instants when reference light, which is generated by reflecting the light emitted by the light source via a reference plane, reaches the linear array photoelectric detector are obtained.

In addition to obtaining the target light which is generated by reflecting the light emitted by the light source via the thin medium, it is needed to obtain the time instants when the reference light, which is generated by reflecting the light emitted by the light source via the reference plane, reaches the linear array photoelectric detector. The time instants may be obtained by the linear array photoelectric detector. It should be understood that, the reference plane described above may be a reflecting mirror.

In step S3, first optical distances and second optical distances corresponding to the target light and the reference light are calculated based on the obtained time instants when the target light and the reference light reach the linear array photoelectric detector, and the number of bright and dark fringes in interference fringes are obtained by a signal processing module through using a predetermined calculation method.

After the time instants when the target light, which is generated by reflecting the light emitted by the light source via the thin medium, reaches the linear array photoelectric detector and the time instants when the reference light, which is generated by reflecting the light emitted by the light source via the reference plane, reaches the linear array photoelectric detector are obtained, it is needed to calculate the first optical distances and the second optical distances corresponding to the target light and the reference light based on the obtained time instants when the target light and the reference light reach the linear array photoelectric detector, and the number of bright and dark fringes in interference fringes are obtained by a signal processing module through using a predetermined calculation method.

It should be noted that, the process of obtaining the number of bright and dark fringes in the interference fringes by the signal processing module through using the predetermined calculation method is described in detail in subsequent embodiments, which is not described in detail here.

It should be understood that, the obtained reference light may transmit a lens array and is then received by the linear array photoelectric detector, the linear array photoelectric detector records a time period from a time instant of turning on the light source to a time instant when the reference light reaches the linear array photoelectric detector, and transmits the time period to the signal processing module.

In step S4, a difference between the number of the bright and dark fringes in the interference fringes and the standard number of bright fringes and dark fringes in interference fringes is calculated; and it is determined that there is a foreign body on a surface of the thin medium in a case that the difference is greater than a predetermined threshold.

After the number of the bright and dark fringes in the interference fringes is obtained by the signal processing module through using the predetermined calculation method, it is needed to calculate the difference between the number of the bright and dark fringes in the interference fringes and the standard number of bright fringes and dark fringes in interference fringes by using a predetermined method; and it is determined that there is a foreign body on the surface of the thin medium in a case that the difference is greater than the predetermined threshold. It should be understood that, the predetermined threshold described above is determined based on an oldest thin medium and a standard thin medium by using a method of maximum difference. It should be noted that, the number of the bright and dark fringes in the interference fringes is interference fringe information obtained for a standard thin medium by step S1 to step S3, before the method for non-contact detection of a thin medium in the embodiment is performed.

It should be understood that, the process of calculating the difference by using the predetermined method described above is described in subsequent embodiments, which is not described in detail here.

In the embodiment, the first optical distances and the second optical distances corresponding to the target light and the reference light are calculated based on the obtained time instants when the target light and the reference light reach the linear array photoelectric detector; the number of the bright and dark fringes in the interference fringes is obtained by the signal processing module by using the predetermined calculation method; the difference between the number of the bright and the dark fringes in the interference fringes and the standard number of bright fringes and dark fringes in interference fringes is calculated; and it is determined that there is a foreign body on the surface of the thin medium in a case that the difference is greater than the predetermined threshold. With the technical solutions described above, the following technical problems are solved: when it is detected whether there is a foreign body on the surface of the thin medium using the existing mechanical thickness measurement device, infrared detection device and ultrasound detection device, it is difficult to detect a thin foreign body on the surface of a banknote effectively due to low measurement accuracy of the mechanical thickness measurement device; only foreign bodies on the surface of the banknote having different directions and different reflection characteristics can be detected due to a narrow application field of the infrared detection device; and the ultrasound detection device has a long measurement wavelength and low measurement accuracy due to using ultrasound as a carrier.

Figure 2:
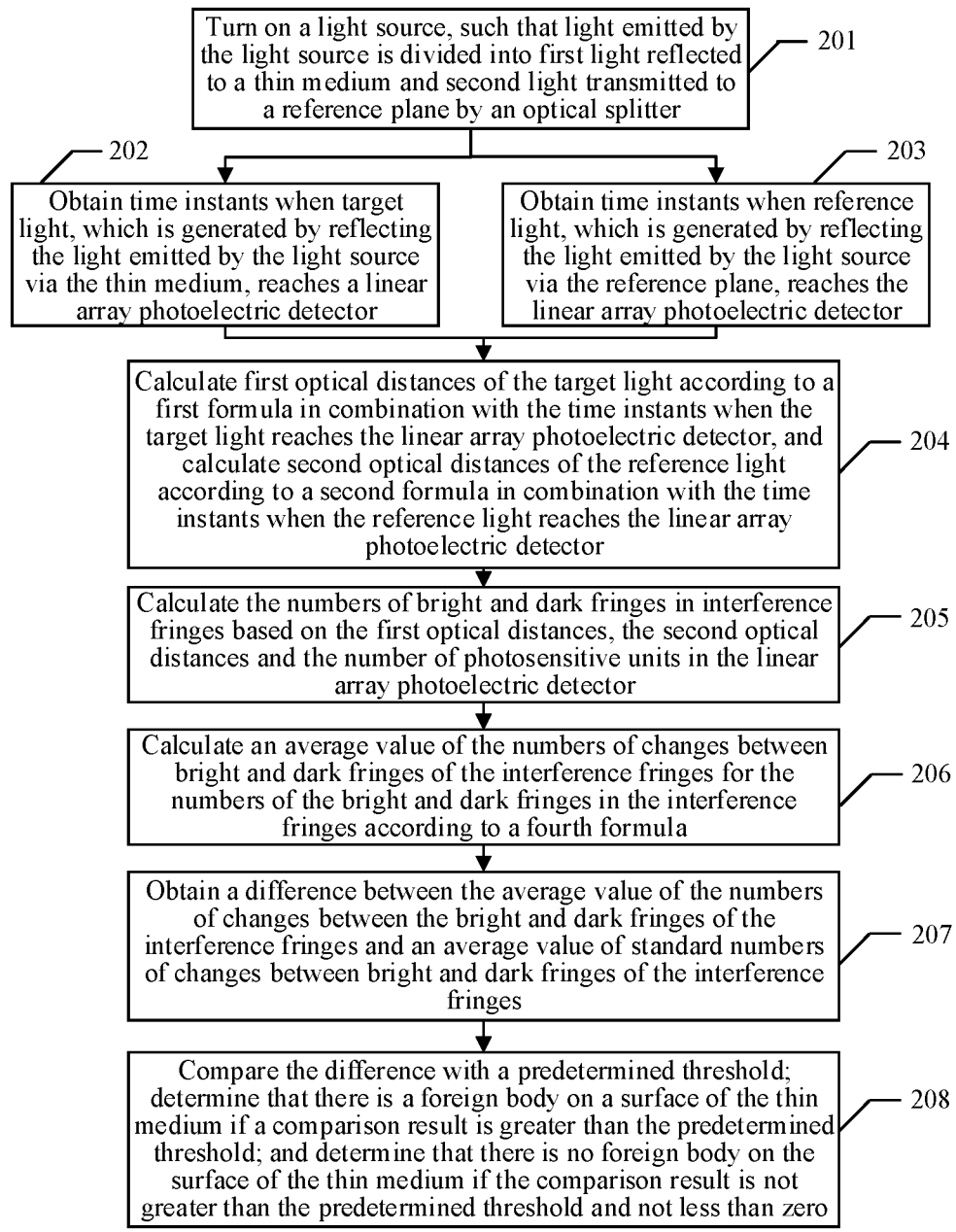
FIG. 2 is a schematic flowchart of a method for non-contact detection of a thin medium according to another embodiment of the present disclosure.

The method for non-contact detection of a thin medium is described in detail above, and the process of obtaining interference fringe information for an electrical signal converted by a photoelectric counter by using a predetermined calculation method and comparing by using a predetermined method is described in detail hereinafter. Referring to FIG. 2, a method for non-contact detection of a thin medium is provided according to another embodiment of the present disclosure. The method includes step S201 to step S208 in the following.

In step S201, a light source is turned on such that light emitted by the light source is divided into first light reflected to the thin medium and second light transmitted to a reference plane by an optical splitter.

In the embodiment, when it is detected whether there is a foreign body on a surface of the thin medium such as a banknote, first it is needed to turn on the light source such that the light emitted by the light source is divided into first light reflected to the thin medium and second light transmitted to the reference plane by the optical splitter. The light source described above may be a laser light source, and may be further a linear array laser light source.

It should be understood that, the first light is reflected by the thin medium to generate target light, and the second light is reflected back to the optical splitter by the reference plane and is reflected by the optical splitter to generate reference light.

It should be noted that, subsequent detections on the thin medium may be performed during transferring by a banknote transmission mechanism, which is not described in detail here.

In step S202, time instants when the target light, which is generated by reflecting the light emitted by the light source via the thin medium, reaches a linear array photoelectric detector are obtained.

In the embodiment, when the light emitted by the light source is divided into the first light reflected to the thin medium and the second light transmitted to the reference plane by the optical splitter, first it is needed to obtain the time instants when the target light, which is generated by reflecting the light emitted by the light source via the thin medium, reaches the linear array photoelectric detector. The time instants may be obtained by the linear array photoelectric detector. The light source described above may be a laser light source, and may further be a linear array laser light source.

It should be noted that, the acquired target light may transmit a lens array and is then received by the linear array photoelectric detector, the linear array photoelectric detector records a time period from a time instant of turning on the light source to a time instant when the target light reaches the linear array photoelectric detector and transmits the time period to a signal processing module.

In step S203, time instants when the reference light, which is generated by reflecting the light emitted by the light source via the reference plane, reaches the linear array photoelectric detector are obtained.

In addition to obtaining the target light which is generated by reflecting the light emitted by the light source via thin medium, it is needed to obtain the time instants when the reference light, which is generated by reflecting the light emitted by the light source via the reference plane, reaches the linear array photoelectric detector. The time instants may be acquired by the linear array photoelectric detector. It should be understood that, the reference plane described above may be a reflecting mirror.

It should be noted that, the obtained reference light may transmit a lens array and is received by the linear array photoelectric detector, the linear array photoelectric detector records a time period from a time instant of turning on the light source to a time instant when the reference light reaches the linear array photoelectric detector, and transmits the time period to the signal processing module.

In step S204, first optical distances of the target light are calculated according to a first formula in combination with the time instants when the target light reaches the linear array photoelectric detector, and second optical distances of the reference light are calculated according to a second formula in combination with the time instants when the reference light reaches the linear array photoelectric detector.

After the time instants when the target light, which is generated by reflecting the light emitted by the light source via the thin medium, reaches the linear array photoelectric detector and the time instants when the reference light, which is generated by reflecting the light emitted by the light source via the reference plane, reaches the linear array photoelectric detector are obtained, it is needed to calculate the first optical distances of the target light according to the first formula in combination with the time instants when the target light reaches the linear array photoelectric detector and calculate the second optical distances of the reference light according to the second formula in combination with the time instants when the reference light reaches the linear array photoelectric detector.

It should be noted that, the first formula described above for calculating the first optical distances is $\Delta_1 = ct_1$, and the second formula for calculating the second optical distances is $\Delta_2 = ct_2$.

t1 indicates a time period from a time instant of turning on the light source to a time instant when the target light reaches the linear array photoelectric detector, and t2 indicates a time period from the time instant of turning on the light source to a time instant when the reference light reaches the linear array photoelectric detector. It should be understood that, c described above is the speed of light.

In step S205, the numbers of bright and dark fringes in interference fringes are calculated based on the first optical distances, the second optical distances and the number of photosensitive units in the linear array photoelectric detector.

After the first optical distances of the target light are calculated according to the first formula and the second optical distances of the reference light are calculated according to the second formula, it is needed to calculate the numbers of the bright and the dark fringes in the interference fringes based on the first optical distances, the second optical distances and the number of the photosensitive units in the linear array photoelectric detector according to the third formula.

It should be understood that, the third formula described above may be $$K(M, N) = \frac{\Delta_2 - \Delta_1}{\lambda_0},$$

where K(M, N) indicates the number of changes between the bright and dark fringes of the interference fringes, M indicates the total number of rows scanned by a light signal from the light source, N indicates the number of photosensitive units in the linear array photoelectric detector, and $\lambda_0$ indicates a wavelength of the light source.

It should be noted that, the number of changes of the interference fringes indicates the numbers of changes between the bright and the dark fringes in the interference fringes, and the interference fringe is a laser interference phenomenon generated due to change of an optical distance difference. The laser interference refers to a phenomenon occurred when two or more optical waves having a same frequency, a same vibration direction and a same constant phase difference meet in an overlapped region of a space. When the laser interference occurs, a light field intensity is enhanced in some areas all the time and is weakened in other areas all the time, forming stable strength distribution, i.e., forming interference fringes which change between brightness and darkness according to a certain law. The interference fringe is a trajectory formed by points having the same optical distance difference in two paths of light, and the optical distance difference refers to a difference of optical distances of two paths of light of an illumination device. The change of bright fringes and dark fringes generated due to the laser interference mainly depends on an optical distance difference of two beams rather than a difference of geometric journeys of the two beams. The optical distance refers to a corresponding journey that light transmits in vacuum in a time period, and the corresponding journey is calculated according to a journey that light transmits in a medium in the same time period. An optical distance in a material with a certain refractive index is equal to a product of the refractive index and a propagation distance in the material. When the optical distance difference of the interference device changes with time, a light field intensity received at a fixed point changes alternately between strong and weak. The number of change of interference fringes is well known for those skilled in the art.

In step S206, an average value of the numbers of changes between the bright and dark fringes of the interference fringes for the numbers of changes between the bright and dark fringes of the interference fringes is calculated according to a fourth formula.

After the numbers of the bright and dark fringes of the interference fringes are calculated based on the first optical distances, the second optical distances and the number of photosensitive units in the linear array photoelectric detector, it is needed to calculate the average value of the numbers of changes between the bright and dark fringes of the interference fringes for the numbers of changes between the bright and the dark fringes in the interference fringes according to the fourth formula.

It should be noted that, the fourth formula for calculating the average value of the numbers of changes between the bright and dark fringes of the interference fringes may be $$\Phi_2 = \frac{\sum_{i=1}^{M} \sum_{j=1}^{N} K(M, N)}{M \times N}.$$

In step S207, a difference between the average value of the numbers of changes between the bright and dark fringes of the interference fringes and an average value of the numbers of changes between bright and dark fringes of interference fringes is obtained.

After the average value of the number of changes between the bright and dark fringes of the interference fringes for the numbers of changes between the bright and dark fringes of the interference fringes is calculated according to the fourth formula, it is needed to obtain the difference between the average value of the numbers of changes between the bright and dark fringes of the interference fringes and the average value of the numbers of changes between bright and dark fringes of interference fringes.

It should be understood that, the standard number of bright fringes and dark fringes in interference fringes may be obtained by performing step 201 to step 206 on a standard thin medium such as a standard undamaged banknote and pre-stored in the signal processing module described above.

In step 208, the difference is compared with a predetermined threshold; it is determined that there is a foreign body on a surface of the thin medium in a case that a comparison result is greater than the predetermined threshold; and it is determined that there is no foreign body on the surface of the thin medium in a case that the comparison result is not greater than the predetermined threshold and not less than zero.

After the difference between the average value of the numbers of changes between the bright and dark fringes of the interference fringes and the average value of the numbers of changes between bright and dark fringes of interference fringes is obtained, it is needed to compare the difference with the predetermined threshold; it is determined that there is a foreign body on the surface of the thin medium in a case that the comparison result is greater than the predetermined threshold; and it is determined that there is no foreign body on the surface of the thin medium in a case that the comparison result is not greater than the predetermined threshold and not less than zero.

It should be noted that, the predetermined threshold described above may be a conclusion value obtained by those skilled in the art from a well-known condition and obtained by experience and experiments, or may be an empirical value for those skilled in the art or a conclusion value obtained by experiments. Further, the predetermined threshold is determined based on an oldest thin medium and a standard thin medium by using a method of maximum difference. For example, in a case that the thin medium is a currency note, for multiple oldest banknotes, an average value of the numbers of changes between bright and dark fringes of the interference fringes of the oldest banknotes is determined according to step 202 to step 206 described above; a difference between the average value and the number of changes between bright and dark fringes of the interference fringes in the standard interference fringe information mentioned in step 207 is calculated by using a method of maximum difference, where the difference is the predetermined threshold described above.

In the embodiment, the whole calculation process may be performed by a signal processing module, and the process is well known for those skilled in the art, which is not described in detail here.

In the embodiment, the first optical distances and the second optical distances corresponding to the target light and the reference light are calculated based on the obtained time instants when the target light and the reference light reach the linear array photoelectric detector; the number of the bright and dark fringes in the interference fringes is obtained by the signal processing module through using the predetermined calculation method; the number of the bright and dark fringes in the interference fringes is compared with the standard number of bright and dark fringes in interference fringes; and it is determined that there is a foreign body on the surface of the thin medium in a case that a comparison result is greater than the predetermined threshold. With the above technical solutions, the following technical problems are solved: when it is detected whether there is a foreign body on the surface of the thin medium using the existing mechanical thickness measurement device, infrared detection device and ultrasound detection device, it is difficult to detect a thin foreign body on the surface of a banknote effectively due to low measurement accuracy of the mechanical thickness measurement device; only foreign bodies on the surface of the banknote having different directions and different reflection characteristics can be detected due to a narrow application field of the infrared detection device; and the ultrasound detection device has a long measurement wavelength and low measurement accuracy due to using ultrasound as a carrier, thereby further improving measurement sensibility and measurement accuracy.

Referring to FIG. 3, a device for non-contact detection of a thin medium is provided according to an embodiment of the present disclosure. The device includes:

a light source 1, an optical splitter 2, a reference plane 3, a linear array photoelectric detector 6, a signal processing module 4 and a thin medium 5. It should be noted that, the light source 1 is a linear array laser light source and the reference plane 3 is a planar reflecting mirror.

The light source 1, the optical splitter 2 and the reference plane 3 are located at a same horizontal line.

The signal processing module 4, the linear array photoelectric detector 6, the optical splitter 2 and the thin medium 5 are located at a same vertical line.

The linear array photoelectric detector 6 is located between the signal processing module 4 and the optical splitter 2.

The optical splitter 2 is sloped.

It should be noted that, FIG. 3 only shows a schematic structural diagram of positions of the light source 1, the optical splitter 2, the reference plane 3, the signal processing module 4 and the thin medium 5 in a space according to the embodiment, the light source 1, the optical splitter 2, the reference plane 3, the linear array photoelectric detector 6, the signal processing module 4 and the thin medium 5 may be integrally arranged in the device for non-contact detection of a thin medium, or the light source 1, the optical splitter 2, the reference plane 3, the signal processing module 4 and the thin medium 5 may be independent structures supported by different supporting parts, which is not limited here.

In the embodiment, the light source 1, the optical splitter 2 and the reference plane 3 are arranged at the same horizontal line and the signal processing module 4, the linear array photoelectric detector 6, the optical splitter 2 and the thin medium 5 are arranged at the same vertical line, such that the time instants when the target light and the reference light reach the linear array photoelectric detector are obtained; the first optical distances and the second optical distances corresponding to the target light and the reference light are calculated; the number of bright and dark fringes in the interference fringes is obtained by the signal processing module 4 through using the predetermined calculation method; the number of the bright and dark fringes in the interference fringes is compared with the standard number of bright fringes and dark fringes in interference fringes by using a predetermined method; and it is determined that there is a foreign body on the surface of the thin medium in a case that a comparison result is greater than the predetermined threshold. With the above technical solutions, the following technical problems are solved: when it is detected whether there is a foreign body on the surface of the thin medium using the existing mechanical thickness measurement device, infrared detection device and ultrasound detection device, it is difficult to detect a thin foreign body on the surface of a banknote effectively due to low measurement accuracy of the mechanical thickness measurement device; only foreign bodies on the surface of the banknote having different directions and different reflection characteristics can be detected due to a narrow application field of the infrared detection device; and the ultrasound detection device has a long measurement wavelength and low measurement accuracy due to using ultrasound as a carrier.

The structure of the device for non-contact detection of a thin medium is described in detail above, and additional structures are described in detail hereinafter. Referring to FIG. 4, a device for non-contact detection of a thin medium is provided according to another embodiment of the present disclosure. The device includes:

a light source 1, an optical splitter 2, a reference plane 3, a signal processing module 4 and a thin medium 5. It should be noted that, the light source 1 is a linear array laser light source and the reference plane 3 is a planar reflecting mirror.

The light source 1, the optical splitter 2 and the reference plane 3 are located at a same horizontal line.

The signal processing module 4, the linear array photoelectric detector 6, the optical splitter 2 and the thin medium 5 are located at a same vertical line.

The linear array photoelectric detector 6 is located between the signal processing module 4 and the optical splitter 2.

The optical splitter 2 is sloped.

According to the embodiment, the device may further include:

an external frame 9, where the light source 1 and the reference plane 3 are arranged on two inner walls of the external frame 9, a transparent component 7 placed below the thin medium 5 is arranged on top of the external frame 9, an inner groove 10 is provided at inner bottom of the external frame 9, the linear array photoelectric detector 6 is arranged within the inner groove 10, and the signal processing module 4 is arranged at bottom of the external frame 9;

the transparent component 7, such as glass, which is placed below the thin medium 5 and may be connected to an upper portion of the external frame 6 via a clamping component such as a holder;

a lens array 8 installed between the linear array photoelectric detector 6 and the optical splitter 2, where, the linear array photoelectric detector 6 is installed above the signal processing module 4 and configured to record time instants when the target light and the reference light reach the linear array photoelectric detector 6 respectively after the light source is turned on.

The light source 1 is configured to emit light to the optical splitter 2, and the optical splitter 2 divides the light into first light reflected to the thin medium 5 and second light transmitted to the reference plane 3.

The thin medium 5 is configured to reflect the first light to the signal processing module 4 to extract a signal.

The reference plane 3 is configured to reflect the second light back to the optical splitter 2 and the optical splitter 2 guides the second light to the signal processing module 4 to extract a signal.

How components of the device for non-contact detection of a thin medium in the embodiment are connected is described in detail hereinafter.

The light source 1 is arranged on a left inner side of the external frame 9 and configured to emit narrow-band laser light. The optical splitter 2 is located right below the transparent component 7 and is fixed and connected to the external frame 9 via a holder, and the optical splitter 2 is configured to split and combine the laser light. The reference plane 3, i.e., the planar reflecting mirror, is located on a right side of the optical splitter 2 and arranged on a left inner side of the external frame 9, and the reference plane 3 is configured to reflect vertically incident light and return the light in an original path. The lens array 8 is located right below the optical splitter 2 and connected to the external frame 9, and is configured to converge laser light to the linear array photoelectric detector 6. The linear array photoelectric detector 6 is located below the lens array 8 and arranged in the middle of the inner groove 10, and is configured to measure the number of changes between bright and dark fringes of the interference fringes. The signal processing module 4 is located below the linear array photoelectric detector 6 and configured to process the measured signal. The external frame 9 is configured to fix and connect the linear array laser light source 1, the optical splitter 2, the reference plane 3, the lens array 8, the linear array photoelectric detector 6 and the signal processing module 3. The transparent component 7 is located right above the external frame 9 and is configured to keep the components inside clean.

In the embodiment, the light source 1, the optical splitter 2 and the reference plane 3 are arranged at the same horizontal line and the signal processing module 4, the linear array photoelectric detector 6, the optical splitter 2 and the thin medium 5 are arranged at the same vertical line, such that the time instants when the target light and the reference light reach the linear array photoelectric detector are obtained; the first optical distances and the second optical distances corresponding to the target light and the reference light are calculated; the number of bright and dark fringes of the interference fringes is obtained by the signal processing module 4 through using the predetermined calculation method; the number of the bright and dark fringes in the interference fringes is compared with the standard number of bright and dark fringes in interference fringes by using a predetermined method; and it is determined that there is a foreign body on the surface of the thin medium in a case that a comparison result is greater than the predetermined threshold. With the above technical solutions, the following technical problems are solved: when it is detected whether there is a foreign body on the surface of the thin medium using the existing mechanical thickness measurement device, infrared detection device and ultrasound detection device, it is difficult to detect a thin foreign body on the surface of a banknote effectively due to low measurement accuracy of the mechanical thickness measurement device; only foreign bodies on the surface of the banknote having different directions and different reflection characteristics can be detected due to a narrow application field of the infrared detection device; and the ultrasound detection device has a long measurement wavelength and low measurement accuracy due to using ultrasound as a carrier.

Those skilled in the art may clearly know that, for convenience and conciseness of description, regarding operation processes of the systems, devices and units described above, one may refer to corresponding processes in the method embodiments described above, which is not described in detail here.

In the embodiments according to the present disclosure, it should be understood that the disclosed systems, devices and methods may be achieved by other manners. The device embodiments described above are only schematic. For example, the units are classified by logical functions, and practically the units may be classified in other ways. For example, multiple units or components may be combined or integrated into another system, some features may be ignored or not implemented. In another point, coupling between each other, direct coupling or communication connection displayed or discussed may be indirect coupling or communication connection via some interfaces, devices or units, which may be electric, mechanical or in other forms.

The units illustrated as separate components may be physically separated or not, and the components displayed as units may be physical units or not, i.e., the components may be located at a same position or may be distributed on multiple network units. The object of the solution of the embodiment may be achieved by selecting a part or all of the units as needed.

In addition, various functional units in various embodiments of the present disclosure may be integrated in one processing unit, various physical units may exist independently from each other, or two or more units may be integrated in one unit. The integrated units described above may be implemented by hardware or software functional units.

In a case that the integrated units are implemented as software functional units and sold or used as independent products, the integrated units may be stored in a computer readable storage medium. Based on such understanding, essential parts, parts contributing to the conventional technology or a part of or all of the technical solutions of the present disclosure may be implemented as a software product. The computer software product is stored in a storage medium and includes several instructions for enabling a computer device (which may be a personal computer, a server or a network device and so on) to perform a part or all of steps in the methods described according to various embodiments of the present disclosure. The storage medium described above includes various types of mediums which may store program codes, for example a USB flash disk, a mobile hard disk, a Read-Only Memory (ROM), a Random Access Memory (RAM), a magnetic disk or a compact disk.

The embodiments described above are only used to illustrate technical solutions of the present disclosure and are not intended to limit the present disclosure. Although the present disclosure is illustrated in detail with reference to the embodiments described above, it should be understood by those skilled in the art that the technical solutions recorded in the embodiments described above may be changed or a part of the technical features may be equivalently replaced. The change and replacement does not cause essences of corresponding technical solutions to depart from the spirit and scope of the technical solutions in the embodiments of the present disclosure.

The invention claimed is:

1. A method for non-contact detection of a thin medium, comprising:
    step S1, obtaining time instants when target light, which is generated by reflecting light emitted by a light source via the thin medium, reaches a linear array photoelectric detector;
    step S2, obtaining time instants when reference light, which is generated by reflecting the light emitted by the light source via a reference plane, reaches the linear array photoelectric detector;
    step S3, calculating first optical distances of the target light according to a first formula $\Delta_1 = ct_1$;
    calculating second optical distances of the reference light according to a second formula $\Delta_2 = ct_2$; and
    calculating number of changes between the bright and dark fringes in the interference fringes according to a third formula $$K(M, N) = \frac{\Delta_2 - \Delta_1}{\lambda_0};$$

wherein, $\Delta_1$ indicates the first optical distances of the target light, $t_1$ indicates a time period from a time instant of turning on the light source to the time instant when the target light reaches the linear array photoelectric detector, $\Delta_2$ indicates the second optical distances of the target light, $t_2$ indicates a time period from the time instant of turning on the light source to the time instant when the reference light reaches the linear array photoelectric detector, K indicates the number of changes between the bright and dark fringes in the interference fringes, M indicates the total number of rows scanned by a light signal from the light source, N indicates the number of photosensitive units in the linear array photoelectrical detector, and $\lambda_0$ indicates a wavelength of the light source;
    step S4, calculating a difference between the number of changes between the bright and dark fringes in the interference fringes and a standard number of changes between bright fringes and dark fringes in interference fringes by using a predetermined method, and determining that there is a foreign body on a surface of the thin medium in a case that the difference is greater than a predetermined threshold;
    step S5, picking out the thin medium which has the foreign body on the surface.

2. The method for non-contact detection of a thin medium according to claim 1, before step S1, further comprising:
    turning on the light source, wherein the light emitted by the light source is divided, by an optical splitter, into first light reflected to the thin medium and second light transmitted to the reference plane, wherein,
    the first light is reflected by the thin medium to generate the target light; and
    the second light is reflected back to the optical splitter by the reference plane and is reflected by the optical splitter to generate the reference light.

3. A device for non-contact detection of a thin medium, comprising a light source, an optical splitter, a reference plane, a linear array photoelectric detector, a signal processing module and the thin medium, wherein
    the light source, the optical splitter and the reference plane are located at a same horizontal line;
    the signal processing module, the linear array photoelectric detector, the optical splitter and the thin medium are located at a same vertical line;
    the linear array photoelectric detector is located between the signal processing module and the optical splitter; and
    the optical splitter is sloped;
    wherein, the light source is configured to emit light to the optical splitter, wherein the optical splitter divides the light into first light reflected to the thin medium and second light transmitted to the reference plane;
    the thin medium is configured to reflect the first light to the signal processing module to extract a signal;
    the reference plane is configured to reflect the second light to the optical splitter, wherein the optical splitter guides the second light to the signal processing module to extract a signal;
    the signal processing module is configured to calculate first optical distances of the target light, to calculate second optical distances of the reference light, to calculate number of changes between the bright and dark fringes of the interference fringes, and to determine that there is a foreign body on the surface of the thin medium; and
    the linear array photoelectrical detector is installed above the signal processing module and configured to record time instants when target light and reference light reach the linear array photoelectric detector respectively after the light source is turned on.

4. The device for non-contact detection of a thin medium according to claim 3, further comprising:

a transparent component placed below the thin medium; and a lens array installed between the linear array photoelectric detector and the optical splitter.

5. The device for non-contact detection of a thin medium according to claim 3, further comprising:

an external frame, wherein the light source and the reference plane are installed on two inner walls of the external frame respectively, the transparent component placed below the thin medium is arranged on top of the external frame, an inner groove is provided at inner bottom of the external frame, and the linear array photoelectric detector is arranged in the inner groove; and the signal processing module is arranged at bottom of the external frame.

6. The device for non-contact detection of a thin medium according to claim 4, further comprising:

an external frame, wherein the light source and the reference plane are installed on two inner walls of the external frame respectively, the transparent component placed below the thin medium is arranged on top of the external frame, an inner groove is provided at inner bottom of the external frame, and the linear array photoelectric detector is arranged in the inner groove; and the signal processing module is arranged at bottom of the external frame.

7. A method for non-contact detection of a thin medium, comprising:

step S1, obtaining time instants when target light, which is generated by reflecting light emitted by a light source via the thin medium, reaches a linear array photoelectric detector;

step S2, obtaining time instants when reference light, which is generated by reflecting the light emitted by the light source via a reference plane, reaches the linear array photoelectric detector;

step S3, calculating first optical distances of the target light according to a first formula $\Delta_1 = ct_1$;

calculating second optical distances of the reference light according to a second formula $\Delta_2 = ct_2$;

calculating a plurality of numbers of changes between the bright and dark fringes in the interference fringes according to a third formula $$K(M, N) = \frac{\Delta_2 - \Delta_1}{\lambda_0};$$

and calculating an average value of the plurality of numbers of changes between the bright and dark fringes of the interference fringes according to a fourth formula $$\Phi_2 = \frac{\sum_{i=1}^{M} \sum_{j=1}^{N} K(M, N)}{M \times N};$$

wherein, $\Delta_1$ indicates the first optical distances of the target light, $t_1$ indicates a time period from a time instant of turning on the light source to the time instant when the target light reaches the linear array photoelectric detector, $\Delta_2$ indicates the second optical distances of the target light, $t_2$ indicates a time period from the time instant of turning on the light source to the time instant when the reference light reaches the linear array photoelectric detector, K indicates the number of changes between the bright and dark fringes in the interference fringes, M indicates the total number of rows scanned by a light signal from the light source, N indicates the number of photosensitive units in the linear array photoelectrical detector, and $\lambda_0$ indicates a wavelength of the light source, $\Phi_2$ indicates the average value of the plurality of numbers of changes between the bright and dark fringes of the interference fringes;

step S4, obtaining a difference between the average value of the plurality of numbers of changes between the bright and dark fringes of the interference fringes and an average value of a plurality of standard numbers of changes between bright and dark fringes of interference fringes; and comparing the difference with a predetermined threshold; determining that there is a foreign body on the surface of the thin medium (5) in a case that a comparison result is greater than the predetermined threshold; and determining that there is no foreign body on the surface of the thin medium (5) in a case that the comparison result is not greater than the predetermined threshold and not less than zero;

step S5, picking out the thin medium which has the foreign body on the surface.

8. The method for non-contact detection of a thin medium according to claim 7, before step S1, further comprising:

turning on the light source, wherein the light emitted by the light source is divided, by an optical splitter, into first light reflected to the thin medium and second light transmitted to the reference plane, wherein, the first light is reflected by the thin medium to generate the target light; and the second light is reflected back to the optical splitter by the reference plane and is reflected by the optical splitter to generate the reference light.

* * * * *